United States Patent [19]

Urry

[11] Patent Number: 5,527,610
[45] Date of Patent: Jun. 18, 1996

[54] ELASTOMERIC POLYPEPTIDE MATRICES FOR PREVENTING ADHESION OF BIOLOGICAL MATERIALS

[75] Inventor: Dan W. Urry, Birmingham, Ala.

[73] Assignees: The UAB Research Foundation; Bioelastics Research, Ltd., both of Birmingham, Ala.

[21] Appl. No.: 246,874

[22] Filed: May 20, 1994

[51] Int. Cl.⁶ .................................................. C08G 69/10
[52] U.S. Cl. .................. 428/373; 428/374; 428/394; 428/395; 428/474.4; 525/432; 528/328; 530/323; 530/324; 530/328; 530/330; 530/350
[58] Field of Search ........................ 525/432; 528/328; 428/373, 374, 394, 395, 474.4

[56] References Cited

U.S. PATENT DOCUMENTS

| | | | |
|---|---|---|---|
| 4,474,851 | 10/1984 | Urry | 428/373 |
| 4,500,700 | 2/1985 | Urry | 528/328 |
| 4,594,409 | 6/1986 | Hayashi et al. | 528/328 |
| 4,783,523 | 11/1988 | Urry et al. | 530/323 |
| 5,250,516 | 10/1993 | Urry | 514/17 |

OTHER PUBLICATIONS

Chemical Abstracts 90:1889, "Coacervation Properties in Sequential Polypeptide Models of Elastin".

Rapaka, et al., (1978) "Coacervation Properties in Sequential Polypeptide Models of Elastin" *Int. J. Peptide Protein Res.* 12:81–92.

*Primary Examiner*—Frederick Krass
*Attorney, Agent, or Firm*—Cooley Godward Castro Huddleson & Tatum

[57] ABSTRACT

The invention provides a bioelastomer comprising tetrapeptide and/or pentapeptide monomeric units of the formula:

$$R_1PGR_2G_n$$

wherein $R_2$ is a peptide-producing residue of alanine or glycine; P is a peptide-producing residue of proline; G is a peptide-producing residue of glycine; $R_2$ is a peptide-producing residue of glycine or alanine; and n is 0 or 1. In a further aspect of the invention, a method is provided for preventing adhesion of biological materials, such as protein, cells, and tissues, by forming a protective layer between a first surface and a second surface using the bioelastomer.

11 Claims, 1 Drawing Sheet

ELASTOMERIC POLYPEPTIDE MATRICES FOR PREVENTING ADHESION OF BIOLOGICAL MATERIALS

This invention as made with U.S. Government support under contract N00014-90-C-0265 awarded by the Department of the Navy. The Government has certain rights in this invention.

INTRODUCTION

1. Technical Field

The present invention relates to the field of biocompatible structural materials and coatings which are suitable for in vivo applications.

2. Background

Bioelastomeric polypeptides are a relatively new development that arose in the laboratories of the present inventor and are disclosed in a series of previously fried patents and patent applications. For example, U.S. Pat. No. 4,474,851 describes a number of tetrapeptide and pentapeptide repeating units that can be used to form a bioelastic polymer. Specific bioelastic polymers are also described in U.S. Pat. Nos. 4,132,746, 4,187,852, 4,589,882, and 4,870,055. U.S. Pat. No. 5,064,430 describes polynonapeptide bioelastomers. Bioelastic polymers are also disclosed in related patents directed to polymers containing peptide repeating units that are prepared for other purposes but which can also contain bioelastic segments in the final polymer: U.S. Pat. Nos. 4,605,413, 4,976,734, and 4,693,718, entitled "Stimulation of Chemotaxis by Chemotactic Peptides"; U.S. Pat. No. 4,898,926, entitled "Bioelastomer Containing Tetra/Pentapeptide Units"; U.S. Pat. No. 4,783,523 entitled "Temperature Correlated Force and Structure Development of Elastin Polytetrapeptide"; U.S. Pat. Nos. 5,032,271, 5,085,055, and 5,255,518, entitled "Reversible Mechanochemical Engines Comprised of Bioelastomers Capable of Modulable Temperature Transitions for the Interconversion of Chemical and Mechanical Work"; U.S. Pat. No. 4,500,700, entitled "Elastomeric Composite Material Comprising a Polypeptide"; and U.S. Pat. No. 5,250,516 entitled "Bioelastomeric Materials Suitable for the Protection of Wound Repair Sites." A number of other bioelastic materials and methods for their use are described in pending U.S. patent applications including: U.S. Ser. No. 07/184,873, filed Apr. 22, 1988, now U.S. Pat. No. 5,336,256 entitled "Elastomeric Polypeptides as Vascular Prosthetic Materials"; U.S. Serial No. 07/962,608, filed Oct. 16, 1992, now abandoned entitled "Bioelastomeric Drug Delivery System"; and U.S. Ser. No. 08/187,441, filed Jan. 24, 1994, entitled "Photoresponsive Polymers". All of these patents and patent applications are herein incorporated by reference, as they describe in detail bioelastomers and/or components thereof and their preparation. This information can be used in preparing and using the compositions and methods of the present invention, which are prepared from different specific monomeric units but can be prepared (and in many cases used, although with the advantages described herein) in the same manner as previously prepared bioelastomers.

The prior art bioelastic materials have been proposed for a number of uses and apparatuses, as indicated by the general subject matter of the applications and patents set forth above. The bioelastic compositions and machines respond to pressure, chemical, light, and/or thermal changes in the environment by phase transitions (e.g., viscosity or turbidity changes) or by contraction or relaxation to reversibly transduce these energies into mechanical work (for example, as described in U.S. Pat. No. 5,226,292).

The bioelastomers were developed based on investigations into the natural bioelastomer elastin. Elastin is comprised of a single protein containing a serial alignment of alanine-rich, lysine-containing cross-linking sequences alternating with glycine-rich hydrophobic sequences. With the entire bovine sequence known, the most striking hydrophobic sequences, both from the standpoint of length and of composition, are one that contains a polypentapeptide (PPP) and one that contains a polyhexapeptide (PHP). Elastin also contains several tetrapeptide (TP) units. As a result of work conducted by the present inventors, the polypentapeptide of elastin when cross-linked has been found to be elastomeric and the polyhexapeptide thereof has been found to be non-elastomeric and appears to provide a means for aligning and interlocking the chains during elastogenesis. It has also been found that the elastin polypentapeptide and polytetrapeptide are both conformation-based elastomers that develop entropic elasticity and strength on undergoing an inverse temperature transition to form a regular β-turn containing dynamic structure.

A typical biological elastic fiber is comprised of a large elastin core covered with a fine surface layer of microfibrillar protein. Elastin is formed upon cross-linking of the lysine residues of tropoelastin. The repeating elastin pentapeptide has the formula $(VPGVG)_n$, while the repeating hexapeptide has the formula $(VAPGVG)_n$, where n varies depending upon the species. The tetrapeptide unit has the formula (VPGG). These sequences, of course, utilize the standard one-letter abbreviation for the constituent amino acids.

It has been found that these polypeptides are soluble in water below 25° C. but on raising the temperature they associate reversibly to form a water-containing viscoelastic phase in the polypentapeptide (PPP) and polytetrapeptide (PTP) cases, whereas in the polyhexapeptide (PHP) case, they associate irreversibly in water to form a granular precipitate, which usually requires the addition of trifluoroethanol to the aggregate for redissolution. On cross-linking, the former (PPP) and (PTP) have been found to be elastomers, whereas PHP is not elastomeric.

For purposes of clarification, it is noted that the reversible temperature elicited aggregation, which gives rise upon standing to a dense viscoelastic phase, is called coacervation. The viscoelastic phase is called the coacervate, and the solution above the coacervate is referred to as the equilibrium solution.

Most importantly, cross-linked PPP, PTP and analogs thereof at fixed length exhibit elastomeric force development at different temperatures spanning a range of up to about 75° C. depending upon several controllable variables. Moreover, these cross-linked elastomers develop near maximum elastomeric force over a relatively narrow temperature range. Thus, by synthesizing bioelastomeric materials having varying molar amounts of the constituent pentamers and tetramers together with such units modified by hexameric repeating units, and by choosing a particular solvent to support the initial viscoelastic phase, it is possible to rigorously control the temperature at which the obtained bioelastomer develops elastomeric force.

In general, the process of raising the temperature to form the above elastomeric state is an inverse temperature transition resulting in the development of a regular non-random structure, unlike typical rubbers, which utilizes, as a characteristic component, hydrophobic intramolecular interactions. The regular structure is proposed to be a β-spiral, a loose water-containing helical structure with β-turns and spacers between turns of the helix which provides hydrophobic contacts between helical turns and has suspended peptide segments. These peptide segments are free to undergo large amplitude, low frequency rocking motions called librations. This mechanism of elasticity is called the librational entropy mechanism of elasticity (or is sometimes referred to as resulting from damping of internal chain dynamics on extension). The elastomeric force of these various bioelastomers develops as the regular structure thereof develops. Further, a loss of regular structure by high temperature denaturation results in loss of elastomeric force. These polymers can be prepared with widely different water compositions, with a wide range of hydrophobicities, with almost any desired shape and porosity, and with a variable degree of cross-linking by selecting different amino acids for the different positions of the monomeric units and by varying the cross-linking process, e.g. chemical, photochemical, enzymatic, irradiative, used to form the final product.

The bioelastomeric polymers have considerable potential for use in medical and other applications, as they can be modified in structure to provide a number of different biological properties. One type of desired property, which has been previously achieved to some extent, is low adhesion of proteins, cells, and other biological components. Adhesions accompanying the healing of wounds, whether due to surgery or other trauma, give rise to many disadvantageous effects. For example, peritoneal cavity adhesions after surgery lead to intestinal obstruction and necessitate recurring operations. Furthermore unwanted adhesions themselves pose problems during recurrent operations. In another example, tendon adhesions often compromise tendon surgery and repair. Still again, adhesion often arise after heart by-pass surgery, sometimes even resulting in adhesion of heart muscle to the back of the breast bone. Pericardial adhesions often arise in heart surgery. In biological situations involving implantation of exogenous material into a tissue, as in the use of permanent artificial joints or temporary implants such as catheters, surgical drains, and shunts, cell adhesion and resulting cell growth can impair the functioning of the implant or of the surrounding tissue. Clearly, it would be advantageous to find a suitable material that could function as a perfect insulator material for isolating wound repair sites from adhesions whether between layers of abdominal and thoracic walls, between repair sites within the abdomen or thorax, within the hand, wrist, foot, ankle, and other joints, or between the skin and body stroma, as well as for protecting implanted materials from stimulating cell adhesion. Such a material would have to satisfy many prerequisites. For example, it would be necessary that such a material would match the compliance of the soft tissue site of application. The material would also need to be biologically inert (or at least degradable to non-toxic products) and be obtainable in different forms, such as elastomeric sheets, foams or powders, that would provide sufficient ease of handling for each particular application. Of course, such a material would also have to be readily sterilizable as well as being biocompatible and eliciting insignificant immunogenic and antigenic responses in the host. By biological compatible is meant that the material in final form will not harm the organism or cell into which it is implanted to such a degree that implantation is as harmful or more harmful than absence of treatment with the indicated material. The same properties described above would also be advantageous in a material for the protection of burn areas and to facilitate repair of the damaged tissue.

Materials exhibiting these properties have been described in U.S. Pat. No. 5,250,516. However, room for improvement remains, and it would be beneficial to provide a material for medical applications that fully meets all of the above requirements and furthermore provides a surface to which biological materials, whether cells or macromolecules such as proteins or polynucleotides, do not adhere in an in vivo or in vitro situation, especially one in which blood or a blood component such as serum is present.

SUMMARY OF THE INVENTION

Accordingly, it is an object of the present invention to provide an elastomeric material which is compatible with and similar to the soft tissue at wound sites and which is also biodegradable, if at all, to non-toxic components.

It is also an object of the invention to provide a material that is available in different physical forms, such as sheets, gels, foams, or powders, or that can be grafted onto another surface to provide ease of handling for various applications.

It is also an object of the invention to provide a process for isolating wound repair sites or implants to effect a more salutary wound healing process.

According to the present invention, the foregoing and other objects are obtained by providing an improved biocompatible material comprising a polymer made from tetrapeptide and or pentapeptide monomers of the formula $R_1PGR_2G_n$ wherein $R_1$ is a peptide-producing residue of alanine or glycine; P is a peptide-producing residue of proline; G is a peptide-producing residue of glycine; $R_2$ is a peptide-producing residue of glycine or alanine; and n is 0 or 1. The polymer can be present as a copolymer containing a mixture of tetrameric and pentameric units and further can contain other monomeric units in some embodiments of the invention.

BRIEF DESCRIPTION OF THE DRAWINGS

The invention will be better understood by reference to the following detailed description of specific embodiments together with the figures that form part of this specification, wherein.

DESCRIPTION OF SPECIFIC EMBODIMENTS

Figure 1:
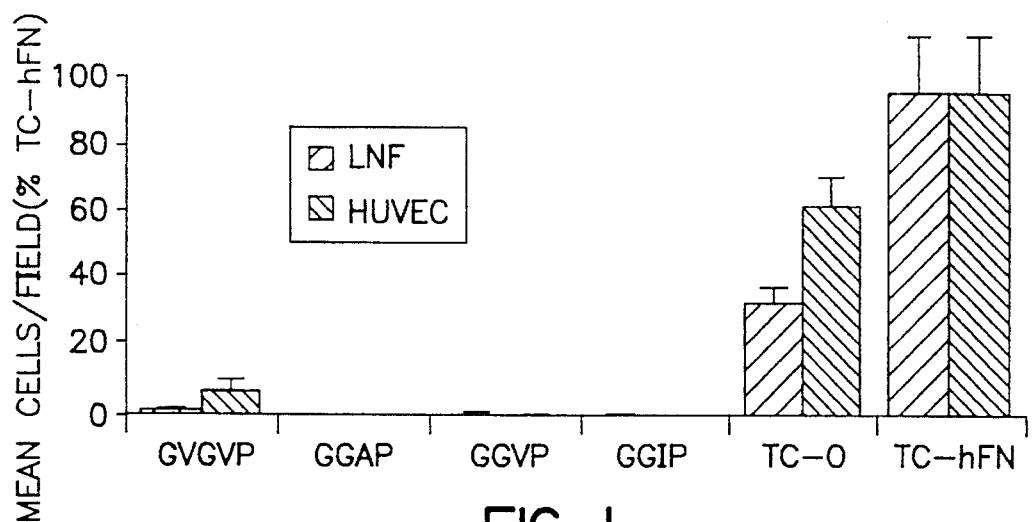
FIG. 1 is a schematic diagram showing the mean number of LNFs and HUVECs adhering to $X^{20}$-poly(GGAP), $X^{20}$-poly(GGVP), $X^{20}$-poly(GGIP), and $X^{20}$-poly(GVGVP) matrices after 3 h in the presence of 0.1% BSA. TC-O and TC-hFN represent uncoated and human fibronectin coated (10 μg/mL) tissue culture plastic substrata. The vertical bars represent one standard error.

In its broadest aspect, the bioelastomers of the present invention comprise tetrapeptide and/or pentapeptide units of the formula $R_1PGR_2G_n$ where $R_1$ and $R_2$ are peptide-producing residues of alanine or glycine, P is a peptide-producing residue of proline, G is a peptide-producing residue of glycine, and n is 0 or 1. These units are generally present in the polymer in an amount sufficient to provide elastomeric properties and to adjust the development of elastomeric force of the bioelastomer to a predetermined temperature, as has been described for previous bioelastomers.

These polymers differ from specific polymers previously disclosed in the laboratories of the inventor in several important, although subtle, ways. For example, it was previously discovered and reported that a polymer prepared from the repeating pentameric unit —APGVG— did not have elastomeric properties but was instead granular, a property that ruled out the use of such polymers in the types of situations contemplated for the polymers of the present invention. This was thought to result from the presence of an alanine residue at position 1 of the β-turn, which was thought to disrupt this structure that is essential for elasticity. However, it now appears as a result of the investigations leading to the present invention that an alanine (or glycine) can be present at position 1 without disrupting the β-turn if there is an alanine or glycine present at position 4. Additionally, the presence of an alanine or glycine at position 4, instead of a more hydrophobic amino acid residue, such as valine or isoleucine, is useful in preventing the adhesion of macromolecular species such as proteins and nucleic acids to surfaces prepared from bioelastic polymers. Adhesion of such biological macromolecules and other biological materials to a surface is often preliminary to adhesion of cells and tissues. Thus the polymers of the invention are useful in form barriers to cell and tissue adhesion in a number of biological situations.

There appears to be no upper limit to the molecular weight of useful polymers of the invention except that imposed by the processes of making these polymers. Polymers containing up to about 250 pentamers have been synthesized in *E. coli* using recombinant DNA methods. Typical polymers contain at least 5, preferably at least 10, more preferably at least 20, tetrapeptide or pentapeptide monomers, and because of poor solubility in aqueous solvents, which are desirable for biological uses, usually contain fewer than 1000, usually fewer than 500, of such units.

It should be noted that bioelastomeric polypeptide chains containing the repeating units can have tetrapeptide or pentapeptide "monomers" that are permutations of the basic sequence (e.g., poly-GGAP vs. poly-APGG). If the polymer is not synthesized using the pentapeptide "monomers", but rather is synthesized by sequential adding of amino acids to a growing peptide, such as in the case of an automatic peptide synthesizer or in genetic production, the designation of the repeating unit is somewhat arbitrary. Moreover, "incomplete units" can flank regions of, for example, a polytetramer so that GG-(APGG)$_{10}$-A may equally well be thought of as G-(GAPG)$_{10}$-GA or (GGAP)$_{10}$-GGA). Designation of a material as, for example, poly-WXYZ is therefore intended to encompass all same-sequence permutations (poly-XYZW, poly-YZWX, and poly-ZWXY), unless otherwise stated or clear from the context.

The bioelastomer can be uncross-linked or cross-linked, depending on the manner of its ultimate use. For example, if the bioelastomer is used as a surface coating on a second material that provides appropriate mechanical properties, cross-linking is not necessary to proved mechanical strength. Cross-linking provides mechanical strength and rigidity to the polymer, and increasing amounts of cross-linking are appropriate for increasing demands of rigidity. Typical amounts of cross-linking provide one cross-link for every 5–100 tetrapeptide or pentapeptide units. Methods for cross-linking bioelastomeric polypeptides are known in the art. For example, U.S. Pat. No. 4,589,882, incorporated herein by reference, teaches enzymatic cross-linking by synthesizing block polymers having enzymatically cross-linkable units. These bioelastic polymers are described in the various patents and other documents listed above that arose in the laboratories of the present inventors. Additionally, cross-linking by irradiation is described in detail in nearly all of the prior patents arising from the laboratories of the inventor, which have been incorporated by reference above. Further specific examples are set out below. Polymers described in this specification that are prepared by irradiation cross-linking are identified as, for example, "$X^{20}$-poly(GGAP)," which refers to a polymer prepared from GGAP tetrapeptide units that has been γ-irradiated with a 20 Mrad dose of cobalt-60 radiation to form the cross-links which result in an insoluble matrix.

In order to obtain high molecular weight polymers in good yields, a number of approaches are available. When producing polymers by chemical synthesis, care should be taken to avoid impurities, because small levels of impurities can result in termination of the polymerization process or in racemerization that can alter the physical properties of the resulting polymer, but there are otherwise no particular problems of synthesis. Different bioelastomer unit permutations have been prepared and polymerized with different coupling methods, and one such technique is described in detail in the examples below. Peptide unit purity is important in obtaining a material with suitable physical properties, since small changes in the preparation of the pentamers can result in a transition temperature that varies as much as 15° C. (25° C.–40° C.). This variance is important to consider since a polymer that has a 25° C. transition temperature will form a very good cross-linked elastomeric matrix, while a preparation having a 40° C. transition temperature will not cross-link to form an elastomeric matrix. The solution of this potential problem is simply to purify the components used to prepare the peptide.

Synthesis of the bioelastomeric repeating units of the present invention is straightforward and easily accomplished by a peptide chemist or by standard methods in microbial fermentation. In order to prepare poly(GGXP), where X is Gly, Ala, Val or Ile, several different synthetic coupling strategies have been used. In one approach, a 2+2 strategy was used in which the dipeptides Gly-Gly and X-Pro were coupled together, while in a second approach, a step-wise addition strategy starting at the C terminus was used. The step-wise addition approach gave a better yield and a product with a lower transition temperature as compared to the 2+2 approach.

An alternative to the organic synthesis of protein-based polymers is a biosynthetic approach using current recombinant DNA methodologies. Using this approach, a gene encoding the desired peptide sequence is constructed, artificially inserted into, and then translated in a microbial host organism. The resulting protein can then be purified, often in large amounts, from cultures grown in fermentation reactors. Molecular biology techniques known in the art are used to manipulate the genetic information (i.e., DNA sequences) for their effective expression in the appropriate host organism (see, for example, Sambrook et al., Molecular Cloning: A Laboratory Manual, Second Edition, Cold Spring Harbor, N.Y. (1989)). The primary tools that make this possible are known in the art and include enzymes capable of cleaving, joining, copying and otherwise modifying polynucleotides.

In addition, vectors allowing the introduction of this information into the host organism in a suitable manner for expression are also known in the art. A detailed example of the production of poly-VPGVG is set out in McPherson et al., "Production and Purification of a Recombinant Elastomeric Polypeptide, G-(VPGVG)$_{19}$-VPGV, from *Escherichia coli*," Biotechnol. Prog., 1992:347–352, a publication arising from the laboratory of the present inventor. This publication can be used as guidance for genetic-based production of the material of the present invention.

The basic polymer of the invention, in its simplest form, is prepared as a homopolymer from one of the eight basic monomers, namely APGA, APGG, GPGA, GPGG, APGAG, APGGG, GPGAG, and APGGG. Of these, polymers formed from tetrapeptide units or from units in which the first amino acid residue is alanine are preferred, particularly those formed from APGG. Either random or block copolymers prepared from the monomeric units are also useful for the indicated purposes but are less preferred when an equivalent homopolymer has the desired physical properties, simply because of the greater complexity of synthesis.

In some embodiments the present invention uses the specified tetrapeptide and pentapeptide units to form a matrix which is then modified in a variety of ways to obtain additional properties. A matrix formed from the indicated monomeric units is particularly useful for biological applications, since the biological inertness of the matrix provides an excellent background in which other activities can be either maximally effected or measured. Considerable variations in the amino acids that are present at various locations in the resulting polymer is possible as long as the multiple β-turns with intervening suspended bridging segments are retained in order to preserve elasticity and the sequences do not promote adhesion more than is desired for a particular application. For this reason it is preferred that at least 50% of the polypeptide is formed from the indicated monomeric units, more preferably at least 70%, even more preferably at least 90%. Nevertheless, it is possible to prepare polypeptides in which these mothomeric units are interspersed throughout a larger polypeptide that contains peptide segments designed for other purposes. For example, the bioelastomer can contain naturally occurring sequences which are components of connective tissue. These can be insertions of, for example, single amino acids between monomeric units, substitutions of one amino acid for another in an occasional monomer, or inclusion of different polypentapeptide, polyhexapeptide or polytetrapeptide sequences which can be added either in parallel or in sequence to increase strength, elastic modulus and ease of handling. The bioelastic units of the invention can be attached to or interspersed among other types of molecules, which molecular units can impart functions to the polymer such as biological activity, chemotaxis, protease, or nuclease susceptibility. Such molecules include peptides, proteins, nucleic acid, DNA, RNA, carbohydrates and lipid chains. As disclosed in earlier U.S. Patents, additional properties, e.g. strength, specific binding, are imported to bioelastomeric materials by compounding the repeating elastic units to a second material with greater strength or with the desired property as disclosed in U.S. Pat. Nos. 4,474,851 and 5,064,430. Such compounding can be oriented in the backbone of the polymer by preparing copolymers in which bioelastic units that form β-turns are interspersed among polymer units providing a desired property e.g. cell adhesion sequences for appropriate tissue cells. These sequences can be added covalently and sequentially or as side chains to provide for the desired cell adhesion (or lack thereof) as in a tendon sheath or in a fascia or in burn covers. The ratio of these other sequences to the monomer residue can range from 1:2 to 1:5000. Preferably the ratio is 1:10 to 1:100. The upper limit on the number and kind of substituents is also influenced by the ability of the elastic polymer to fold/assemble properly to attain a beta-spiral in the relaxed state.

When considering bioelastomers of the invention, it will be apparent that artificial materials are intended and that there is no intention to claim elastin or other natural materials. As discussed previously for bioelastomers, the defined structure of the artificial bioelastomers of the invention allow full and complete design of the physical properties of the bioelastomers, rather than having to rely on the less controllable properties that would exist for material prepared from natural products.

The location of a random or systematic substituent in the polymer, with respect to the monomer residue side-chain position, is not critical so long as the beta-turn is not prevented from forming in the relaxed state. Preferred positions for the various peptides of the invention are as taught in the patents and pending applications from the laboratory of the present inventor in this area, which have been incorporated by reference.

In addition, additional amino acid residues can be optionally interspersed within the polymer to enable covalent linkage of the bioelastic polymer to a surface, although simple coating of a surface with a solution of the polymer is satisfactory for many situations, especially when only short-term protection of the surface is necessary. For example, cysteine can be introduced into the polymer to allow for linkage via disulfide bridges to a surface or lysine can be introduced for enzymatic linkage to a surface. In a preferred embodiment, one or more of these linking groups are present at one or both of the terminal ends of a polypeptide strand, either at the ultimate terminus or within the 5 % of residues at the terminus, rather than in the interior of a polypeptide strand. When the polymer is prepared using genetic techniques, the reactive linking groups are preferably at the N-terminal portion of the molecule. In such embodiments, covalent attachment occurs between a functional group in the bioelastomer and a functional group in the material that forms the surface, which can itself be a different bioelastomer, such as those described in the prior art. Attachment of bioelastomers to surfaces and various coating processes for surfaces are described in various of the patents cited in the Background section of this specification and are not essential parts of the present invention.

As discussed supra, it has been found that the elastic polypentapeptide and polytetrapeptide bioelastomers are both conformation-based elastomers that develop entropic elasticity and strength on undergoing an inverse temperature transition to form a regular β-turn containing dynamic structure. In the presence of serum, considerable but sub-maximal cell attachment occurs using bioelastomers known in the art, e.g., X$^{20}$-poly(GVGVP), poly(GGIP), and poly(G-GVP), many of which, particularly poly(GGVP), are quite close in structure to the polymers of the present invention. In contrast, however, the present bioelastomers result in no cell attachment even in the presence of serum, making the bioelastomers of the invention prepared from the selected group of monomers a more effective physical barrier for prevention of adhesions than the previously used materials.

The elastomeric polypeptides of the present invention have the ability to control adhesions at wound repair sites even in the presence of serum. Moreover, the polypeptides are biodegradable and biocompatible as a soft tissue implant, are readily sterilizable, and furthermore can be formed in cross-linked sheets or strips, varying from a gelatinous to a teflon-like consistency. It is even possible to prepare these materials in a deformable foam-like state with or without cross-linking. Also, when efficacious, the sequential polypeptide could be applied as a powder, which on absorbing water produces a sticky viscoelastic gel-like material.

In the presence of much serum, a greater functional specificity can be achieved by adding specific functional sequences to the bioelastomers of the present invention, as described above. This property is relevant to the development of a surgical adhesion preventative biomaterial. For example, for cardiopulmonary by-pass procedures where there can be substantially more bleeding than in the contaminated peritoneal cavity model, the bioelastomers can also provide a suitable non-adhesive matrix for the testing of incorporated adhesion-promoting sequences in the presence of serum without the background interference of serum protein binding resulting in cell adhesion. Another relevant application could be to form the intimal lining of a vascular prosthesis.

For example, by adding to the protein-based polymer a cell attachment sequence such as Gly-Arg-Gly-Asp-Ser-Pro (GRGDSP) from fibronectin to result in, for example, the elastic matrix $X^{20}$-poly[40(GGAP),(GRGDSP)], a matrix which was refractory to cell adhesion now promotes cell adhesion, cell spreading and growth to confluence. Importantly, this means that cells can migrate into and attach to the matrix and be subjected to, and also to sense the tensional forces to which the matrix is subjected in its functional role. It is now appreciated, for example, that the cyclic stretching to which a vascular wall is subjected induces the vascular wall cells to turn on the genes which result in elaboration of the macromolecules required to maintain and to rebuild the tissue required to sustain such tensional forces. This has been called tensegrity, and it provides the basis for developing a temporary functional scaffolding into which the natural cells can migrate, attach, and remodel into the natural required tissue.

The cell adhesion of $X^{20}$-poly(GVGVP) in the presence of serum is probably due to the association or absorption of adhesion proteins such as fibronectin and vitronectin from the serum as occurs with other biomaterial. Equally, the lack of cell adhesion to the present bioelastomers in the presence of serum would seem to be due to the lack of association or absorption of adhesion-promoting serum components. Although not wishing to be bound by a particular hypothesis, the inventor believes that the observed correlation of increased cell adhesion with increased hydrophobicity of the polytetrapeptide-based matrices in the presence of serum suggests that the serum components responsible may associate by hydrophobic interactions and that at a certain reduced level of matrix hydrophobicity, for example that of $X^{20}$-poly(GGAP), their association is insufficient to support cell attachment.

Another aspect of the invention is directed to a method for substantially preventing cellular adhesion by forming a protective layer between a first surface and a second surface using the present bioelastomers. The surface referred to can be a tissue culture vessel material, e.g. glass, plastic, or cells, tissue, dried body fluids at wound repair sites, or a mechanical implant such as a catheter, surgical drain, or shunt. The bioelastomer would generally form a layer of at least 10 Å, preferably at least 10 Å, in thickness on the surface and can optionally be linked to the surface, as described above. Alternatively one of the surfaces can be entirely formed from a material of the invention.

Studies of the efficacy of various materials as a barrier in the prevention of adhesions employing a contaminated peritoneal model indicates the utility of the polymers of the invention for cardio-pulmonary bypass products. With the propensity of such biopolymers to act innocuously in the body and to be refractory to formation of adhesions coating these polymers onto catheters, leads and tubings that would reside in the body for days, weeks and even months would result in a more ready removal and to do so with minimal damage to tissues that would have been in contact with such temporary devices.

The invention now being generally described, the same will be better understood by reference to the following examples, which are provided for purposes of illustration only and are not to be considered limiting of the invention unless so specified.

EXAMPLES

1. Peptide Synthesis

The synthesis and cross-linking of poly(GVGVP) have been described in U.S. Pat. No. 4,783,523. The syntheses of poly(IPGG) has been described in U.S. Pat. No. 5,250,516. The tetrapeptide monomer Boc-GGAP-OH was synthesized by the stepwise solution phase method described below and then formed into polymers.

In the Examples, the following abbreviations will be used: Boc, tertbutyloxycarbonyl; Bzl, benzyl; DMF, dimethylformamide; DMSO, dimethylsulfoxide; EDCI, 1-(3-dimethylaminopropyl)-3-ethylcarbodiimide; HOB, 1-hydroxybenzotriazole; IBCF, isobutyl-chloroformate; N-methylmorpholine; ONp, p-nitrophenylester; TFA, trifluoroacetic acid. All Boc amino acids and HOBt were purchased from Advanced ChemTech, (Louisville, Ky.). EDC was obtained from Bachere, Inc. (Torrance, Calif.).

Boc-Ala-Pro-OBzl (I)

Boc-Ala-OH (56.76 g, 0.3 mole) dissolved in acetonitrile (500 mL) and cooled to 0° C. before adding NMM (32.97 mL). The solution was cooled to −15°±1° C. and isobutyl chloroformate (41.01 mL) was added slowly under stirring while maintaining the temperature at −15° C. After stirring the reaction mixture for 10 min at this temperature, HOBt (40.56 g, 0.3 mole) was added. The reaction mixture was stirred for an additional 10 min and a pre-cooled solution of HC;●H-Pro-OBzL (72.5 g, 0.3 mole) and NMM (32.97 mL) in DMF (600 mL) were added slowly. After 20 min, the pH of the solution was adjusted to 8 by the addition of NMM and the reaction was continued overnight. The solvent was removed under reduced pressure and the residual DMF solution was poured into about 2000 mL of ice-cold 90% saturated $KHCO_3$ solution and stirred for 30 min. Since the peptide did not precipitate out, it was extracted into $CHCl_3$, which was washed with water, 20% citric acid, and water, and dried over $Na_2SO_4$, and the solvent was washed with water, 20% citric acid, and water, before drying over $Na_2SO_4$, and removing solvent under reduced pressure. The resulting oil was recrystallized from ether/petroleum ether. The crystals were filtered, washed with petroleum ether, and dried to obtain 79.9 g (yield, 70.75 %) of I. $R^1_f$, 0.5; $R^2_f$ 0.61.

Boc-Gly-Ala-Pro-OBzl (II)

Boc-Ala-Pro-OBzl (75.3 g, 0.2 mole) was deprotected by stirring for 1.5 h. in 4.2 N HCl in dioxane. Excess HCl and dioxane were removed under reduced pressure, triturated with ether, faltered, washed with ether, and dried (yield 100%). A solution of Boc-Gly-OH (35.04 g, 0.2 mole) and HOBt (27.02 g, 0.2 mole) in DMF was cooled to −15° C. with stirring and EDCI (38.34 g, 0.2 mole) was added. After 20 rain, a pre-cooled solution containing the above hydrochloride salt and NMM (21.98 mL, 0.2 mole) was added and the reaction mixture was stirred overnight at room temperature. The mixture was evaporated to a thick oil which was dissolved in $CHCl_3$. This solution was extracted with water, 10% citric acid, water, 5 % $NaHCO_3$, water, and dried over $Na_2SO_4$. The solvent was removed under reduced pressure and the resulting oil was crystallized from ether/petroleum ether. The solid was filtered, washed with petroleum ether, and dried to obtain 76.2 g (yield 87.88%) of II. $R^1_f$ 0.39; $R^2_f$ 0.44.

Boc-Gly-Gly-Ala-Pro-OBzl (III)

Compound II (65.03 g, 0.15 mole) was deblocked with HCl/dioxane and coupled to Boc-Gly-OH (26.3 g, 0.15 mole) using EDCI with HOBt in the same manner as that described for II to give 63.2 g (yield 85.9%) of III $R^1_f$ 0.3; $R^2_f$ 0.46.

Boc-Gly-Gly-Ala-Pro-ONp (IV)

Boc-Gly-Gly-Ala-Pro-OBzl (30.0 g, 0.061 mole) was dissolved in glacial acetic acid (300 mL) and 3.0 g of 10% Palladium on activated charcoal was added. This mixture was hydrogenated at 40 psi for 6 h. The reaction mixture was filtered through celite and the solvent was removed in vacuum. The resulting residue was triturated with ether, faltered, washed with ether, and dried to obtain Boc-Gly-Gly-Ala-Pro-OH.

This acid was dissolved in pyridine (200 mL) and reacted with Bis-PNPC (1.5 equiv.). When the reaction was complete, as monitored by TLC, the solvent was removed under reduced pressure. The residue was taken into $CHCl_3$ and washed with water, 10% citric acid, water, 5 % $NaHCO_3$, water, and dried over $Na_2SO_4$. The solvent was removed under reduced pressure, triturated with ether, faltered, washed with ether, and dried to obtain 18.3 g (yield 57.52%) of IV. $R^1_f$ 0.22; $R^2_f$ 0.38; $R^3_f$ 0.48.

Poly(Gly-Gly-Ala-Pro) (V)

Boc-Gly-Gly-Ala-Pro-ONp (18.0 g, 0.035 mole) was deblocked using TFA and a one-molar solution of the TFA salt in DMSO was polymerized for 14 days using 1.6 equiv. of NMM as base. The polymer was dissolved in pyrogen-free water, dialyzed using 3500 mol. wt. cut-off dialysis tubing and lyophilized. The product was base-treated with 1 N NaOH (2 equiv. per tetramer), dialyzed using 50 kD mol. wt. cut-off tubing for 8 days and lyophilized to obtain 5.02 g (yield 51.5 %) of V.

To verify structure and purity, the intermediate and final products were checked by TLC, carbon-13 NMR spectroscopy, and amino acid analysis. The presence of all requisite peaks and the absence of extraneous peaks are required to verify the synthesis. Thin layer chromatography (TLC) was performed on silica gel plates obtained from Whatman, Inc., with the following solvent systems: $R^1_f$ $CHCl_3$:$CH_3OH$: $CH_3COOH$; $R^2_f$ $CHCl_3$:$CH_3COOH$ (90:10:3); $R^3_f$ $CHCl_3$:$CH_3OH$: $CH_3COOH$ (85:15:3). The compounds on TLC plates were detected by UV light by spraying with ninhydrin or chlorine/toluidine.

2. Preparation of the Cross-linked Matrices

Poly(GGVP) and poly(GGAP) were dissolved separately in pyrogen-free water at a concentration of 600 mg/mL. The solutions were then placed in a mold and centrifuged with the temperature maintained at 25° C. for 1 h. The temperature was then raised to 40° C. and centrifuged for 8 more hours. Poly(GGIP) was also dissolved in pyrogen-free water at a concentration of 400 mg/mL. The solution was centrifuged with the temperature maintained at 10° C. over a period of 5 h and 30° C. over a period of 15 h. The coacervate phase was then checked for uniformity. If they did not have irregularities such as bubbles, they were then γ-irradiated with a 20 Mrad dose of cobalt-60 radiation to form the cross-links which resulted in an insoluble matrix. The molds were then opened in a laminar flow hood using sterile conditions and placed until use in PBS containing 100 u/mL penicillin, 100 μg/mL streptomycin, and 2.5 μg/mL amphotericin-B at 4° C.

3. Cell Culture

Bovine ligamentran nuchae fibroblasts (LNFs) were cultured in Dulbecco's modified Eagle medium containing 10% fetal bovine serum, 2 nM L-glutamine, 0.1 mM nonessential amino acids, 100 u/mL penicillin, and 100 μg/mL streptomycin as described by Long et al. in Biochem. Biophys, Acta. 968,300–311(1988).

Human umbilical vein endothelial cells (ItUVECs) at passage 1 were bought from Endotech Corporation, (Indianapolis, Ind.). Cells were cultured in Medium 199 containing 25 mM HEPES, 20% fetal bovine serum, 2 nM L-glutamine, 13.2 μL/mL Endo-Ret HI-GF (Endotech) endothelial cell growth supplement, 100 u/mL penicillin, 100 μg/mL streptomycin, and 2.5 μg/mL amphotericin-B. Tissue culture flasks for HUVECs were precoated with 2 % bovine gelatin (Sigma) at 7.5 μl/cm².

Both LNFs and HUVECs were passaged by trypsinization and were used for experiment at passage 8 or earlier.

4. Adhesion Assay

The assay and apparatus has been described by Nicol et al., J. Biomed. Mater. Res., 26, 393–413 (1992). Cells were harvested using 0.05 % trypsin/0.53 mM EDTA (Gibco) and then treated with 0.2 mg/mL soybean trypsin inhibitor. The cell density plated on the test matrices was 100 cells/mm². Cell concentration was adjusted to $0.32 \times 10^5$/mL and 50 μL aliquots were plated into glass cylinders containing 50 μL of appropriate medium over discs of the test matrices. Three replicates were used for each experimental condition. The apparatus was incubated for 3 or 20 h to allow cell adhesion, after which the matrices were gently rinsed in PBS, pH 7.2, and then flexed in 3.5 9 paraformaldehyde in PBS, pH 7.2. Phase contrast microscopy was then used to count and classify the adherent cells. The area of one field of view counted was 1.2 sq. mm. and five such fields were counted for each replicate. The total area plated over was 15.9 sq. mm. for each replicate. Thus, 37 9 of the total area plated was counted. The target plated cell density of 100 cells/sq. mm. was chosen as suitable for individual cell recognition, quantitation, and classification. To normalize variations in the actual density of cells plated between experiments, the results are given as the percent of the appropriate positive control.

To examine the adhesion of LNFs and HUVECs to the cross-linked elastomeric matrices alone, the cells were plated onto the test matrices in the absence of serum and in the presence of 0.1% BSA. After incubation for 3 h the matrices and control substrata were rinsed and then fixed, as described above. It was found (FIG. 1) that neither cell type was able to adhere to any of the three polytetramer-based matrices and that cell adhesion to $X^{20}$-poly(GVGVP) was extremely poor. The few fibroblasts or endothelial cells which were found adherent to the matrices were rounded and had not spread.

Figure 2:
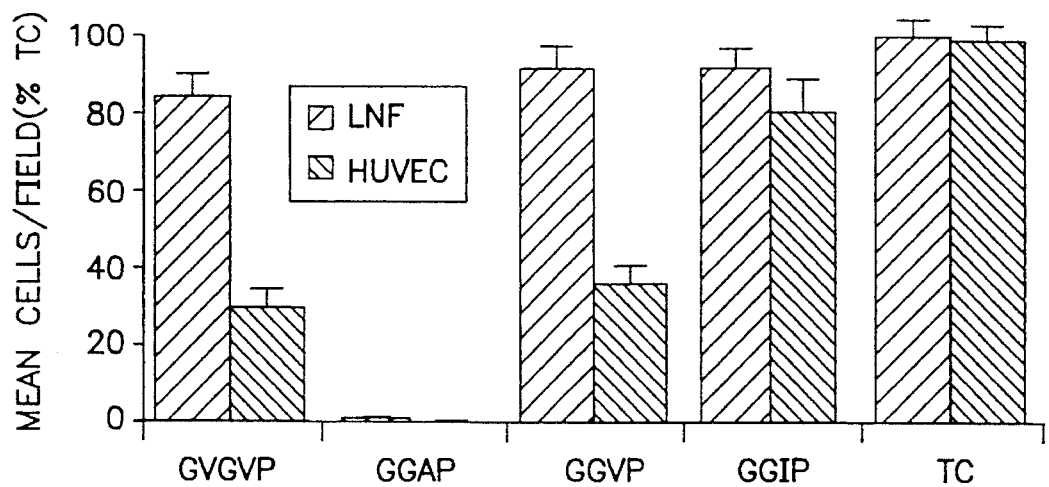
FIG. 2 is a schematic diagram showing the mean number of LNFs and HUVECs adhering to $X^{20}$-poly(GGAP), $X^{20}$-poly(GGVP), $X^{20}$-poly(GGIP), and $X^{20}$-(GVGVP) matrices after 3 h in the presence of 10% fetal bovine serum (LNFs) and 20% fetal bovine serum (HUVECs). TC represents normal tissue culture plastic substratum. The vertical bars represent one standard error.

In the presence of 10% fetal bovine serum, LNFs were found to adhere to $X^{20}$-poly(GVGVP) at near control tissue culture substratum levels after 3 h incubation (FIG. 2). Also, on these matrices the fibroblasts were largely well spread. The fibroblasts failed to attach or spread on the $X^{20}$-poly(GGAP) after 3 h in the presence of serum (FIG. 2). The results for HUVECs plated in the presence of 20% fetal bovine serum (FIG. 2) were similar to those for LNFs except that the relative levels of cell attachment to $X^{20}$-poly(GGVP) and $X^{20}$-poly(GVGVP) were much less. The level of attachment of HUVECs to $X^{20}$-poly(GGIP) was only slightly less than that found for LNFs. No endothelial cell adhesion to $X^{20}$-poly(GGAP) was found (FIG. 2).

Figure 3:
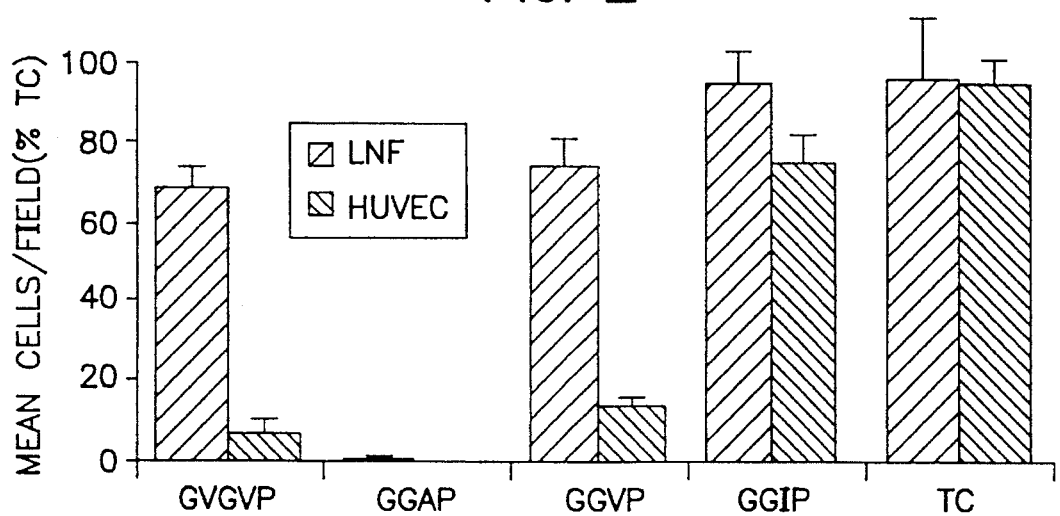
FIG. 3 is a schematic diagram showing the mean number of LNFs and HUVECs adhering to $X^{20}$-poly(GGAP), $X^{20}$-poly(GGVP), $X^{20}$-poly(GGIP), and $X^{20}$-poly(GVGVP) matrices after 20 h in the presence of 10% fetal bovine serum (LNFs) and 20% fetal bovine serum (HUVECs). TC represents normal tissue culture plastic substratum. The vertical bars represent one standard error.

After 20 h of incubation in the presence of serum (FIG. 3), the results found for both LNFs and HUVECs were essentially the same as for 3 h incubation except that the relative levels of cell attachment to the matrices were generally reduced. Again, for both LNFs and HUVECs, the $X^{20}$-poly(GGAP) gave no support for cell adhesion.

The mean residue hydrophobicity of the polytetrapeptide matrices based on the temperature of inverse temperature transition hydrophobicity scale are 37° C. for GGAP, 31.5° C. for GGVP, and 28° C. for GGIP. The lower the temperature the greater the hydrophobicity. It can be seen from FIGS. 2 and 3 that, of the three polytetrapeptide-based matrices in the presence of serum, the least hydrophobic (GGAP) showed the lowest levels of cell adhesion and the most hydrophobic (GGIP) showed the highest levels of cell adhesion. The correlation coefficients for these relationships were −0.92, −0.98, −0.98, and −0.90 for 3 h and 20 h of LNF and 3 h and 20 h of HUVEC attachment, respectively.

5. Biocompatibillty a. The Ames Mutagenicity Test

The Ames test uses five strains of *Sahnonella typhimurium* each containing a specific mutation in the histidine operon. Without the presence of histidine, these five genetically altered strains—TA98, TA100, TA1535, TA1537 and TA1538 will not grow. To study mutagenicity, these five strains are placed in a histidine-free medium where only those able to mutate back to the wild non-histidine dependent type will form colonies. The reversion rate is normally constant. Accordingly, if the introduction of a test article causes at least a two-fold increase in reversion rate, as compared to spontaneous reversion in the presence of negative control (in this case saline), then the test article is considered mutagenic and therefore a possible carcinogen.

The test solution was a 4 mg/ml solution in 0.85% saline of poly(GGAP), equivalently poly(APGG). As seen in TABLE 1, the test article was not found to be mutagenic in this study. In fact, the test article was indistinguishable from the saline negative control. The positive controls were: Dexon for TA98, TA100 and TA1537; sodium azide for TA1535; 2-aminofluorene and 2-nitrofluorene for TA1538, and 2-aminofluorene for TA1 00. Metabolic activation is necessary for 2-aminofluorene to be mutagenic, therefore the 2-aminofluorene was tested on TA100 and TA1538 both with and without S-9 mix. The S-9 mix, which is a microsomal fraction from an appropriately induced rat liver homogenate, was used to detect any mutagenic chemicals present that may require metabolic biotransformation to become active mutagenic forms. The innocuous nature of poly(GGAP) becomes apparent when its reversion rates are compared to those of Dexon which is a sufficiently biocompatible material for regular use as a biodegradable suture material.

b. Cytotoxicity—Agarose Overlay

Confluent monolayers of the L-929 mouse connective tissue cells were grown in culture flasks. Minimum essential medium was prepared, then placed in the culture flasks and allowed to solidify over the cells to form the agarose overlay. A 0.1 ml sample of 40 mg/ml poly(GGAP) in 0.90% saline was dosed neat on a 12.7 mm diameter filter disk which was then placed on the solidified overlay surface. A like filter disk with 0.1 ml of 0.9 % sodium chloride USP solution was used as a USP negative control. The positive control was placed in a 25 sq. cm flask equidistant from the test article on the agarose surface. The flask containing controls and test article was then sealed and incubated for 24 hours at 37° C. After 24 hours the culture was examined. The test article showed no cell lysis or toxicity (a 0 mm zone of lysis) while the negative controls were non-toxic and the positive control was toxic (with a 9 mm zone of lysis). Thus poly(GGAP) was found to be non-toxic to L-929 mouse connective tissue cells.

c. Acute Systemic Toxicity

Five mice were weighed and then injected by an intravenous route with a 40 mg/ml solution of poly(GGAP) in 0.85% saline at a dose of 50 ml/kg. Five other mice were similarly injected with control saline solution. The animals were then observed at 4, 24, 48 and 72 hours. Significant signs of toxicity are mortality, body weight loss of more than 2 g in three or more mice, convulsions or prostration. Slight signs of toxicity would be lethargy or hyperactivity. The mice appeared normal; no signs of toxicity were observed for poly(GGAP).

d. Intracutaneous Toxicity

A 0.2 ml dose of 40 mg/ml solution of poly(GGAP) in 0.9% saline was injected by the intracutaneous route into five separate sites on the right side of the back of two rabbits, on the left side 0.9% sodium chloride USP solution was injected as a control. At 24, 48 and 72 hours the injection sites of the animals were observed for signs of erythema (ER) or edema (ED). In the first study, slight irritation or toxicity was observed. As even a slight irritation was unexpected., the study was rerun at 5 mg/ml. As shown by the results in TABLE 2 neither irritation nor toxicity was observed. Neither erythema (ER) nor edema (ED) was observed.

e. Systemic Antigenicity Study

Solutions of poly(GGAP), equivalently poly(APGG), at a concentration of 40 mg/ml volumes in a 0.9% NaCl test solution, were injected intrapefitoneally at 10 ml/kg body weight three times a week, every other day, until six induction injections were conducted on six guinea pigs. Similarly, three additional guinea pigs were injected intraperitoneally with 0.9% NaCl solution as the control condition. Ten days after the last intrapefitoneal injection, all of the guinea pigs were challenged by an intravenous injection of the poly(G-GAP) solution and then observed for any signs of antigenicity. Significant signs of reaction would be face pawing, eye blinking, lethargy, convulsions and even death. There were no significant reactions to the challenge injection. Therefore, the test article solution would not be considered antigenie in the guinea pig.

f. Dermal Sensitization Study (A Maximization Method)

Fifteen Hanley guinea pigs were used in this study. A 40 mg/ml solution of poly(GGAP) in 0.9% NaCl was the test article. For Induction I, the ten animals to be used were clipped, then received three rows of intradermal injections, 2 per row, in a 2×4 cm area. The injections were 0.1 ml of Freud's Complete Adjuvant (FCA), 0.1 ml of the test article, and 0.1 ml of a 1:1 suspension of the FCA and test article. The five animals to be used as controls at the challenge phase were not induced. For Induction II, one week later the area was reclipped and a 10% sodium lauryl sulfate suspension (SLS) in petrolatum was massaged into the skin to produce a mild acute inflammation. Any SLS suspension remaining after 24 hours was removed. A 2×4 cm of a Whatman No. 3 MM filter paper, saturated with 0.3 ml of the test article, was topically applied and secured with nonreactive tape and an elastic bandage wrapped around the trunk of each animal. The patch was removed after 48 hours.

Next the follow-up challenge was performed at 12 days. The area was again clipped and a nonwoven cotton disk in a Hill Top Chamber@ was saturated with 0.3 ml of the test article, topically applied and held in place for a 24-hour period with semi-occlusive hypoallergenic adhesive tape and an elastic bandage wrapped around the trunk of the animal. The area was observed 24, 48, 72 and 96 hours after patch removal. The test article, poly(GGAP), did not cause delayed contact sensitization in the guinea pig (See TABLE 3). Note: "Background or artifactual reactions (0.5 score) were not counted as evidence of a sensitization response." {NAmSA®}. The 0.5 score occurred with the same frequency in the controls as in the test animals.

g. Rabbit Pyrogen Study

A 0.9 gram portion of poly(GGAP) was reconstituted in 90 ml of sterile nonpyrogenic saline. A single dose of 10 ml/kg was intravenously injected into the marginal ear vein of three rabbits. Rectal temperatures were measured and recorded before injection and every hour for 3 hours afterwards. A maximum rise of 0.1° C. was recorded with a sum in the three animals of 0.2° C. whereas a summed rise of less than 1.4° C. would still be considered non-pyrogenic. Accordingly, the test solution was judged to be non-pyrogenic.

h. Lee-White Clotting Study

A 100 mg portion of poly(GGAP) was reconstituted in 10 ml of 0.9% NaCl solution to yield a 10 mg/ml test solution. 0.5 ml of the test solution was added to six siliconized tubes. These tubes were placed in a 37° C. heat block along with three siliconized tubes (without material) which served as the control. One ml of fresh canine blood was added to each tube.

At timed intervals, the first tube in each set of three was tilted until nearly horizontal. The tilting procedure was repeated at 30 second intervals until the blood clotted. As seen in TABLE 4, the replicate mean is greater in each case for the test article, poly(GGAP), than for the control. Clearly, poly(GGAP) does not shorten the clotting time.

i. Hemolysis Test In Vitro

A clot-free blood sample from a New Zealand White rabbit was collected into an EPTA vacuum tube on the day the test was performed. As usual, four tubes were used in this study: a negative control containing 10 ml of 0.9% sodium chloride USP solution (SC); a positive control containing 10 ml of USP purified water (PW) and 2 tubes each containing 0.2 ml of the test article which is a solution of 40 mg/ml poly(GGAP) in 0.9 % sodium chloride and 10 ml SC containing 0.2 ml of the test article which is again a solution of 4-0 mg/ml poly(GGAP) in 0.9% sodium chloride. To each robe 0.2 ml of rabbit blood was added. The robes were then covered and gently inverted to mix, then placed in a 37° C. water bath for 1 hour. After incubation, the tubes were again gently inverted and the solutions were decanted into centrifuge robes to be centrifuged for 10 minutes at 1000× g. From absorbance values taken at 545 nm the percent hemolysis was determined by the equation:

Test article—SC negative control PW positive control X100-% Hemolysis  (2)

The result in each case was 0% hemolysis; poly(GGAP) was found to be non-hemolytic. The results of the nine biocompatibility tests are summarized in TABLE 5.

TABLE 1

Plate Incorporation Assay for the Ames Mutagenicity Test
Test Article: $X^{20}$-poly(GGAP), Batch CG65PA

| Salmonella typhimurium Tester Strains | TA98 | TAIO0 | TA1535 | TA1537 | TA1538 |
|---|---|---|---|---|---|
| | Number of Revertant Colonies (Average of Duplicate Plates) | | | | |
| Saline (− control) | 82 | 180 | 14 | 8 | 6 |
| Saline test article solution (undiluted) | 57 | 172 | 9 | 6 | 6 |
| Saline w/S-9 (− control) | 92 | 173 | 15 | 11 | 11 |
| Saline w/S-9 test article solution (undiluted) | 74 | 180 | 12 | 7 | 11 |
| Dexon 1 mg/ml (+ control) | 1048 | 1408 | N/A | 247 | N/A |
| Dexon 1 mg/ml w/S-9 (+ control) | 1256 | 1048 | N/A | 1048 | N/A |
| Sodium azide 0.1 mg/ml (+ control) | N/A | N/A | 2752 | N/A | N/A |
| Sodium azide 0.1 mg/ml w/S-9 (+ control) | N/A | N/A | 3176 | N/A | N/A |
| 2-nitrofluorene 1 mg/ml (+ control) | N/A | N/A | N/A | N/A | 2800 |
| 2-nitrofluorene w/S-9 (+ control) | N/A | N/A | N/A | N/A | 2240 |
| 2-aminofluorene 0.1 mg/ml (+ control) | N/A | 184 | N/A | N/A | 11 |
| 2-aminofluorene w/S-9 (+ control) | N/A | 1296 ' | N/A | N/A | 2816 |

TABLE 1-continued

Plate Incorporation Assay for the Ames Mutagenicity Test
Test Article: $X^{20}$-poly(GGAP), Batch CG65PA

| Salmonella typhimurium Tester Strains | TA98 | TA100 | TA1535 | TA1537 | TA1538 |
|---|---|---|---|---|---|
| | Number of Revertant Colonies (Average of Duplicate Plates) | | | | |

N/A = Not Applicable
*Reports from North American Science Associates (NAmSA ®)
In no case was there a two-fold or greater increase in the reversion rate of the tester strains in the presence of the test article solution.

TABLE 2

USP Intracutaneous Toxicity Observations
Test Article: Poly(GGAP)

KEY

| ER | = | ERYTHEMA | ED | = | EDEMA |
|---|---|---|---|---|---|
| 0 | = | None | 0 | = | None |
| 1 | = | Barely Perceptible | 1 | = | Barely Perceptible |
| 2 | = | Well Defined | 2 | = | Well Defined |
| 3 | = | Moderate | 3 | = | Raised 1 mm |
| 4 | = | Severe | 4 | = | Raised > 1 mm |

RESULTS:

| Rabbit No. | | 24 HOURS | | 48 HOURS | | 72 HOURS | |
|---|---|---|---|---|---|---|---|
| | | ER | ED | ER | ED | ER | ED |
| 69235 | Test | 0 | 0 | 0 | 0 | 0 | 0 |
| | Control | 0 | 0 | 0 | 0 | 0 | 0 |
| 69226 | Test | 0 | 0 | 0 | 0 | 0 | 0 |
| | Control | 0 | 0 | 0 | 0 | 0 | 0 |

RATING (TEST - CONTROL)

| 0.0–0.5 | Acceptable |
|---|---|
| 0.6–1.0 | Slight |
| <1.0 | Significant |

*Reports from North American Science Associates (NAmSA ®)
Date Prepared: 2-8-93
Date Injected: 2-8-93
Date Terminated: 2/11/93
Comments: Not Applicable.

TABLE 3

Guinea Pig Sensitization
Dermal Reactions - Challenge
Test Article: $X^{20}$-poly(GGAP), Batch CG65PA.

Hours following patch removal

| Animal No./Group | 24 Right Flank | 48 Right Flank | 72 Right Flank | 96 Right Flank |
|---|---|---|---|---|
| 1 Test | 0 | 0.5 | 0.5 | 0 |
| 2 Test | 0 | 0.5 | 0.5 | 0 |
| 3 Test | 0 | 0 | 0 | 0 |
| 4 Test | 0 | 0 | 0 | 0 |
| 5 Test | 0 | 0 | 0 | 0 |
| 6 Test | 0.5 | 0.5 | 0.5 | 0 |
| 7 Test | 0 | 0 | 0 | 0 |
| 8 Test | 0 | 0 | 0 | 0 |
| 9 Test | 0 | 0 | 0 | 0 |
| 10 Test | 0 | 0 | 0 | 0 |
| 11 Test | 0 | 0 | 0 | 0.5 |
| 12 Test | 0 | 0 | 0 | 0 |
| 13 Test | 0 | 0.5 | 0 | 0 |
| 14 Test | 0 | 0 | 0 | 0 |
| 15 Test | 0.5 | 0.5 | 0.5 | 0 |

Right Flank = test article solution (as received)

TABLE 4

Lee-White Clotting Study
Test Article: Poly(GGAP), Batch CG65PA

| | Series | | |
|---|---|---|---|
| Tubes | A | B | Replicate Mean |
| 1 | 11.5 | 11.5 | 11.5 |
| 2 | 14.5 | 15.0 | 14.8 |
| 3 | 18.0 | 18.0 | 18.0* |

Control:

| | Series | | |
|---|---|---|---|
| Tubes | A | B | Replicate Mean |
| 1 | 9.0 | 7.5 | 8.3 |
| 2 | 14.0 | 12.5 | 13.3 |
| 3 | 15.5 | 15.0 | 15.3* |

*Lee-White coagulation time
NOTE: Time recorded in minutes.

TABLE 5

Summary of Biocompatibility Test Results for Poly(GGAP):
Preparation CG65PA*

| Test | Description | Test System | Results |
|---|---|---|---|
| (1) Ames (Mutagenicity) MG019 | Determine reversion rate to wild type of histidine-dependent mutants | Salmonella typhimurium | non-mutagenic |
| (2) Cytoxicity Agarose overlay MG030 | Agarose overlay determine cell death and zone of lysis | L-929 mouse fibroblast | non-toxic |
| (3) Acute Systemic Toxicity TU012 | Evaluate acute systemic toxicity from an I.V. or I.P. injection | Mice | non-toxic |
| (4) Intracutaneous Toxicity TU013 | Evaluate local dermal irritant or toxic effects by injection | Rabbit | initial test: slight irritation retest - no irritation |
| (5) Systemic Antigenicity TA085 | Evaluate general toxicology | Guinea Pigs | non-antigenic |
| (6) Sensitization (Maximization Method) TA006 | Dermal sensitization potential | Guinea Pigs | non-sensitizing |
| (7) Pyrogenicity TU010 | Determine febrile reaction | Rabbit | non-pyrogenic |
| (8) Clotting Study TA038 | Whole blood clotting times | Dog | Normal clotting time |
| (9) Hemolysis CB037 | Level of hemolysis in the blood | Rabbit blood | non-hemolytic |

*Reports from North American Science Associates (NAmSA ®) where the detailed results are kept in their archives.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A bioelastomer comprising at least 5 repeating tetrapeptide or pentapeptide monomeric units of the formula:

$$R_1PGR_2G_n$$

wherein $R_1$ is a peptide-producing residue of alanine or glycine; P is a peptide-producing residue of proline; G is a peptide-producing residue of glycine; $R_2$ is a peptide-producing residue of glycine or alanine; and n is 0 or 1, wherein said bioelastomer is capable of undergoing an inverse temperature transition to form a regular β-turn-containing dynamic structure.

2. The bioelastomer of claim 1, wherein said bioelastomer is cross-linked.

3. The bioelastomer of claim 1, wherein said bioelastomer is a homopolymer.

4. The bioelastomer of claim 1, wherein said bioelastomer is a block or random copolymer comprising two or more of said monomeric units.

5. The bioelastomer of claim 1, wherein said bioelastomer further comprises up to 30% peptide-bond-forming monomeric units other than said monomeric units.

6. The bioelastomer of claim 1, wherein said $R_1$ is alanine.

7. The bioelastomer of claim 1, wherein $R_2$ is glycine.

8. The bioelastomer of claim 1, wherein a terminal end of said bioelastomer further comprises at least one peptide-forming unit of lysine.

9. The bioelastomer of claim 1, wherein a terminal end of said bioelastomer contain at least one sulfhydryl group.

10. The bioelastomer of claim 1, wherein said bioelastomer is present as a coating on a surface.

11. The bioelastomer of claim 10, wherein said bioelastomer is covalently attached to said surface.

* * * * *